US007937138B2

(12) United States Patent
Liley

(10) Patent No.: US 7,937,138 B2
(45) Date of Patent: May 3, 2011

(54) METHOD OF MONITORING BRAIN FUNCTION

(75) Inventor: David Tibor Julian Liley, Camberwell (AU)

(73) Assignee: Cortical Dynamics Pty Ltd, Scoresby (AU)

( * ) Notice: Subject to any disclaimer, the term of this patent is extended or adjusted under 35 U.S.C. 154(b) by 1373 days.

(21) Appl. No.: 10/542,549

(22) PCT Filed: Jan. 14, 2004

(86) PCT No.: PCT/AU2004/000045
§ 371 (c)(1),
(2), (4) Date: Dec. 22, 2005

(87) PCT Pub. No.: WO2004/064633
PCT Pub. Date: Aug. 5, 2004

(65) Prior Publication Data
US 2006/0135879 A1 Jun. 22, 2006

(30) Foreign Application Priority Data

Jan. 20, 2003 (AU) ................................ 2003900324

(51) Int. Cl.
*A61B 5/04* (2006.01)
(52) U.S. Cl. ........................................................ 600/544
(58) Field of Classification Search .................. 600/544, 600/545
See application file for complete search history.

(56) References Cited

U.S. PATENT DOCUMENTS

| 5,010,891 | A | 4/1991 | Chamoun | |
|---|---|---|---|---|
| 5,083,571 | A | 1/1992 | Prichep | |
| 5,687,291 | A * | 11/1997 | Smyth | 706/10 |
| 5,797,853 | A | 8/1998 | Musha et al. | |
| 6,067,467 | A | 5/2000 | John | |
| 6,549,804 | B1 | 4/2003 | Osorio et al. | |
| 6,658,287 | B1 * | 12/2003 | Litt et al. | 600/544 |
| 7,565,193 | B2 * | 7/2009 | Laken | 600/544 |
| 7,729,755 | B2 * | 6/2010 | Laken | 600/544 |
| 2004/0049484 | A1 * | 3/2004 | Kamba | 707/1 |
| 2004/0101048 | A1 * | 5/2004 | Paris | 375/240.12 |

OTHER PUBLICATIONS

Patomaki L et al: "Tracking of nonstationary EEG with the roots of ARMA models"; Engineering in Medicine and Biology Society, 1995., IEEE 17th Annual Conference Montreal, Que., Canada Sep. 20-23, 1995, New York, NY, USA, IEEE, US, vol. 2, Sep. 20, 1995, pp. 877-878, XP010214737; ISBN: 978-0-7803-2475-6.

Liley D T JA et al: "Drug-induced modification of the system properties associated with spontaneous human electroencephalographic activity"; Physical Review E—Statistical Nonlinear, and Soft Matter Physics—Soft Matter and Biological Physics Nov. 2003 American Physical Society US, vol. 68, No. 5 1, Nov. 2003, pp. 519061-5190615, XP002505701.

Bishop (2002), The Mechatronics Handbook, CRC Press, Chapter 25, section 25.1 System and Signal Analysis. See section 25.1.

Bruce (2001), Biomedical Signal Processing and Signal Modeling, John Wiley & Sons, Inc. Referred to in "Modeling Stochastic Signals as Filtered White Noise", Retrieved from Internet: <bsp.csie.edu.tw/courses/bsp/slidelbsp10.ppt> Entire document.

(Continued)

*Primary Examiner* — Charles A Marmor, II
*Assistant Examiner* — Navin Natnithithadha

(57) ABSTRACT

A method for assessing brain state by analysing mammalian brain electroencephalogram ("EEG") recordings using an eighth order autoregressive and fifth order moving average discrete time equation.

24 Claims, 12 Drawing Sheets

OTHER PUBLICATIONS

Deng (2002), Digital Signal Processing. Retrieved from Internet: www.ee.latrode.edu.au/~dennis/teachinq/EIE32DSP/1.pdf pp. 45 to 52.

Schack B et al (1995). Dynamic Power and Coherence Analysis of Ultra Short-Term Cognitive Processes—A Methodical Study. Brain Topography, 8(2), P:127-136. pp. 129-131.

Schack B et al (1995). Methods of dynamic spectral analysis by self-exciting autoregressive moving average models and their application to analyzing biosignals. Medical & Biological Engineering & Computing, 33, p. 492-498 pp. 493-496.

Tseng et al (1995). Evaluation of parametric methods in EEG signal analysis. Medical, Engineering, Physics, 17, p. 71-78. pp. 72 to 73, pp. 75 to 77. (Inventive step).

Liley D, Cadusch P and Dafilis M, *A spatially continuous mean field theory of electrocortical activity*, Network: Computation in Neural Systems 13 (2002) 67-113.

Liley D, Cadusch P, Gray M and Pradeep N, *Drug inducted modification of system properties associated with spontaneous human encephalographic activity*. Physical Review E 68, 051906 (2003).

L. Patomaki et al., Tracking of nonstationary EEG with the roots of ARMA models, Engineering in Medicine and Biology Society, vol. 2(20), pp. 877-878,Kuopio, Finland.

P. Gannabathula et al., ARMA order selection for EEG—an empirical comparison of three order selectin algorithms, The Annual International Conference of the IEEE Engineering in Medicine & Biology Society, vol. 5, pp. 1686-1687, 1989. Bangalore, India.

\* cited by examiner 8 poles resulting from the 8th order AR & 5th order MA modelling for a single segment of recorded EEG All sets of 8 poles for multiple segments of recorded EEG

METHOD OF MONITORING BRAIN FUNCTION

FIELD OF THE INVENTION

The present invention relates to a method and system for the application of a mathematical model, and in particular a fixed order auto-regressive moving average model, to analyse electroencephalogram ("EEG") signals generated by a subject in order to assess and monitor the subject's brain function under conditions of health, disease and therapeutic intervention.

BACKGROUND OF THE INVENTION

In clinical practice involving alterations in the level of consciousness, such as during the administration of sedatives or general anaesthetic agents, it is important to be able to quantify brain function. Most approaches rely upon the analysis of the brain's surface electrical activity, known as the electroencephalogram or EEG. In general the signal analysis method chosen is based on the statistical properties of the signal being analysed. The more closely matched the method used is to the signal properties, the more reliable, meaningful and accurate the resulting analysis will be. However these signal properties can only be known if the mechanisms and processes responsible for the generation of the signal are also known.

To date none of these analysis methods of the brain's rhythmic electrical activity have incorporated any details of the underlying physiological mechanisms responsible for its genesis. Therefore their ability to measure, and thus monitor, brain function in the clinical setting is limited.

This problem is overcome by the present invention which provides a more rational means of assessing and measuring brain function based on the detailed knowledge of the physiological mechanisms underlying the generation of the brain's surface rhythmic electrical activity.

The theory underlying the present invention considers the cortex of the brain as a single excitable spatial continuum of reciprocally connected excitatory and inhibitory neurons interacting by way of short-ranged (intra-cortical) and long-range (cortico-cortical) connections. As such, the brain is seen as a dynamically evolving entity rather than a synthetic processing unit like a computer.

Based on this theory, the characteristics of alpha rhythms arising as a consequence of the brain's neural connections can be closely represented by a mathematical model, and in particular, a fixed order auto-regressive moving average ("ARMA") model. The present invention derives specific values for the moving average ("MA") and auto-regressive ("AR") orders for the ARMA model based on the electrocortical transfer function. The electrocortical transfer function describes in a mathematical form the origin of the EEG readings taken of a subject.

By applying EEG signals recorded from a subject to the fixed order ARMA model, coefficients can be obtained. To understand how these coefficients can be used to measure brain function, the equations defining the fixed order ARMA model are rewritten in the z-domain (complex domain) and are solved to obtain complex number solutions (called "poles") that are mapped onto the z-plane. These poles represent the state of the brain at the specific point in time when the EEG signal was recorded. Variations in the EEG signal, such as that induced by applying sedatives to the subject, can be detected as variations of the mean location of one or more poles on the z-plane. These variations can be interpreted to measure brain function or to indicate changes in the state of the brain.

By using the brain assessment techniques of the invention, it is possible to monitor the state of a subject in various circumstances. For instance, the method of the invention can be used to monitor the vigilance or alertness of a subject when performing certain tasks such as driving vehicles of various types or controlling critical equipment. In applications of this type, the method can be applied locally so as to warn the driver or controller of a condition which is indicative of a loss of vigilance or alertness so that appropriate action can be taken. The monitoring could be carried out remotely as well as locally.

The method of the invention can be used to monitor a subject whilst sleeping so as to assess various stages in sleep of a subject. The results obtained can be used for determination and/or treatment of sleeping disorders.

Further, the invention can be used to monitor the state of anaesthesia of a patient. In this application it would be typical for the anaesthetist (or an operator) to obtain a display of poles in the said plane prior to administration of the anaesthetic. The method of the invention can then be continued after application of the anaesthetic so that the state of anaesthesia of the patient can be monitored as a function of time by reference to the movement of clusters of poles displayed on display equipment. This provides useful information to the anaesthetist regarding the state of anaesthesia of the subject.

SUMMARY OF THE INVENTION

According to the present invention there is provided a method for assessing brain state by analysing human electroencephalographic recordings using an eighth order autoregressive ("AR") and fifth order moving average ("MA") discrete time model based on a theory of the underlying mechanism of generation of mammalian EEG activity.

The invention also provides a method for assessing brain state by analysing human electroencephalographic recordings using an eighth order autoregressive and fifth order moving average discrete time equation, taking a z-transform for said equations to obtain a z-domain equation, determining poles and zeroes in the solution of the z-domain equation and plotting the poles onto the complex plane.

The invention also provides a method of assessing the state of a mammalian brain including the steps of:

(i) obtaining an electroencephalogram (EEG) from the brain;

(ii) digitising the EEG to define a digitised EEG data signal;

(iii) segmenting the EEG data signal into time frames of fixed length, y[n];

(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;

(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane; and
(xi) assessing the state of the brain by reference to the position and distribution of at least some of said clusters of poles as mapped in the complex plane.

According to the present invention there is also provided a method of assessing the state of a mammalian brain including the steps of:
(i) obtaining an electroencephalogram (EEG) from the brain;
(ii) digitising the EEG to define a digitised EEG data signal;
(iii) segmenting the EEG data signal into time frames of fixed length, y[n];
(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) administering an intervention to the brain;
(xii) repeating steps (i) to (x) at least once;
(xiii) monitoring movement of at least some of said clusters of poles in the complex plane; and
(xiv) assessing the state of the brain by reference to movement of at least some of said clusters of poles as mapped in the complex plane.

According to the present invention there is also provided a method of assessing the state of a mammalian brain including the steps of:
(i) obtaining a first electroencephalogram (EEG) from the brain;
(ii) digitising the EEG to define a digitised EEG data signal;
(iii) segmenting the EEG data signal into time frames of fixed length, y[n];
(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) obtaining a second EEG from said brain at a later time;
(xii) repeating steps (ii) to (x) in relation to the second EEG at least once;
(xiii) monitoring the movement of at least some corresponding clusters of poles in the complex plane derived from the first and second EEGs respectively; and
(xiv) assessing the state of the brain by reference to movement of at least some of said clusters of poles as mapped in the complex plane.

For the methods above, an EEG may be obtained and recorded before it is processed. The recorded EEG can therefore be processed at any time after it has been recorded or it can be used as a reference for comparisons with other EEGs at a future point in time. Alternatively, an EEG may be obtained and processed on-the-fly such that an EEG is repeatedly obtained over consecutive and constant time intervals, and where each time interval may overlap with the immediately preceding time interval. The EEG obtained for each time interval is immediately processed by the methods described above.

Preferably, step (x) is repeated up to 100 times so that there are a plurality of poles in each of the said clusters. Also step (x) may be repeated continuously to track the motion of the poles from each segment.

Preferably further, the method includes a step of taking the centroid of the poles for each cluster of poles, and monitoring and comparing the movement of the centroids.

The present invention further provides a system for performing the above methods. The present invention further provides computer readable media having computer program instructions stored thereon which, when executed by a computer, perform the methods described above.

The invention also provides a method of assessing the efficacy of a cognitively active pharmaceutical agent including the steps of:

(i) obtaining a first electroencephalogram (EEG) from the brain of a subject;
(ii) digitising the EEG to define a digitised EEG data signal;
(iii) segmenting the EEG data signal into time frames of fixed length, y[n];
(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) administering a dose of a cognitively active pharmaceutical agent to the subject;
(xii) obtaining a second EEG from said brain after step (xi);
(xiii) repeating steps (ii) to (x) in relation to the second EEG at least once;
(xiv) monitoring the movement of at least some corresponding clusters of poles in the complex plane derived from the first and second EEGs respectively; and
(xv) assessing the efficacy of the cognitively active pharmaceutical agent by reference to movement of at least some of said clusters of poles as mapped in the complex plane.

The invention also provides a method of assessing the state of vigilance or alertness of a subject including the steps of:
(i) obtaining an electroencephalogram (EEG) from the brain of a subject;
(ii) digitising the EEG to define a digitised EEG data signal;
(iii) segmenting the EEG data signal into time frames of fixed length, y[n];
(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) repeating steps (i) to (x);
(xii) monitoring movement of at least some of said clusters of poles in the complex plane; and
(xiii) assessing the state of vigilance or alertness of the subject by reference to movement of at least some of said clusters of poles as mapped in the complex plane.

The invention also provides a method of assessing the state of sleep of a subject including the steps of:
(i) obtaining an electroencephalogram (EEG) from the brain of a subject;
(ii) digitising the EEG to define a digitised EEG data signal;
(iii) segmenting the EEG data signal into time frames of fixed length, y[n]; (iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) repeating steps (i) to (x);
(xii) monitoring movement of at least some of said clusters of poles in the complex plane; and
(xiii) assessing the state of sleep of the subject by reference to movement of at least some of said clusters of poles as mapped in the complex plane.

The invention also provides a method of assessing the state of anaesthesia of a subject including the steps of:
(i) obtaining an electroencephalogram (EEG) from the brain of a subject while anaesthetised;
(ii) digitising the EEG to define a digitised EEG data signal;

(iii) segmenting the EEG data signal into time frames of fixed length, y[n];
(iv) approximating each digitised time frame by a first equation:

$$y[n] = -\sum_{k=1}^{8} a_k y[n-k] + \sum_{k=0}^{5} b_k u[n-k]$$

(v) solving the first equation to determine coefficients $a_1$ to $a_8$ and $b_0$ to $b_5$;
(vi) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(vii) substituting each of the values of the coefficients into the z-domain equation;
(viii) solving A(z)=0 for z in the second equation to determine the poles;
(ix) plotting the poles in the complex plane;
(x) repeating steps (iv) to (ix) for each frame in the sample to determine clusters of poles in the complex plane;
(xi) repeating steps (i) to (x);
(xii) monitoring movement of at least some of said clusters of poles in the complex plane; and
(xiii) assessing the state of anaesthesia of the subject by reference to movement of at least some of said clusters of poles as mapped in the complex plane.

The invention also provides apparatus for assessing brain state of a subject, the apparatus including a plurality of electrodes for picking up EEG signals from the brain of the subject;
digitising means for converting the EEG signals to a digitised EEG data signal;
computing means for:
(i) segmenting the EEG data signal into time frames of fixed length, y[n];
(ii) approximating each digitised time frame by a first equation:

$$y[n] = -\sum_{k=1}^{8} a_k y[n-k] + \sum_{k=0}^{5} b_k u[n-k]$$

(iii) solving the first equation to determine coefficients $a_1$ to $a_8$ and $b_0$ to $b_5$;
(iv) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

(v) substituting each of the values of the coefficients into the z-domain equation;
(vi) solving A(z)=0 for z in the second equation to determine the poles;
(vii) plotting the poles in the complex plane; and
display means for displaying the poles, to thereby enable assessment of the brain state of the subject by reference to the position and distribution of clusters of said poles.

BRIEF DESCRIPTION OF THE DRAWINGS

Preferred embodiments of the present invention are hereinafter described, by way of example only, with reference to the accompanying drawings, wherein.

DETAILED DESCRIPTION OF PREFERRED EMBODIMENTS OF THE INVENTION

Figure 1:
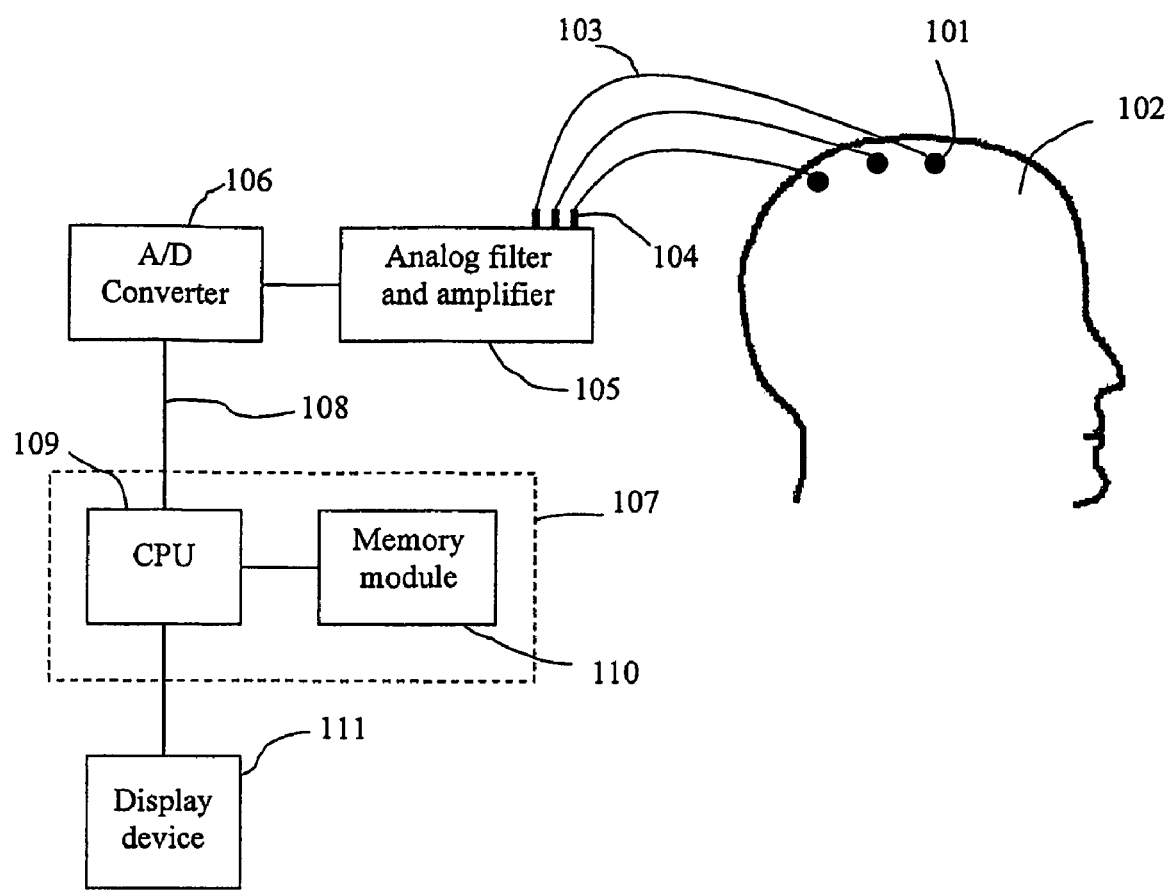
FIG. 1 is a schematic diagram showing one example of the apparatus of the invention.

FIG. 1 is a diagram showing a preferred embodiment of the physical components of the system. The EEG signals are detected by multiple electrodes 101 from the scalp of a subject 102, where the electrodes are positioned preferably arranged according to the international 10:20 standard system with the addition of mid-point electrodes as necessary. Preferably, the EEG signals are recorded referenced to linked ears using 64 scalp electrodes attached to an electrode cap using the nasion as a ground. Other techniques for recording the EEG can also be used.

Figure 10:
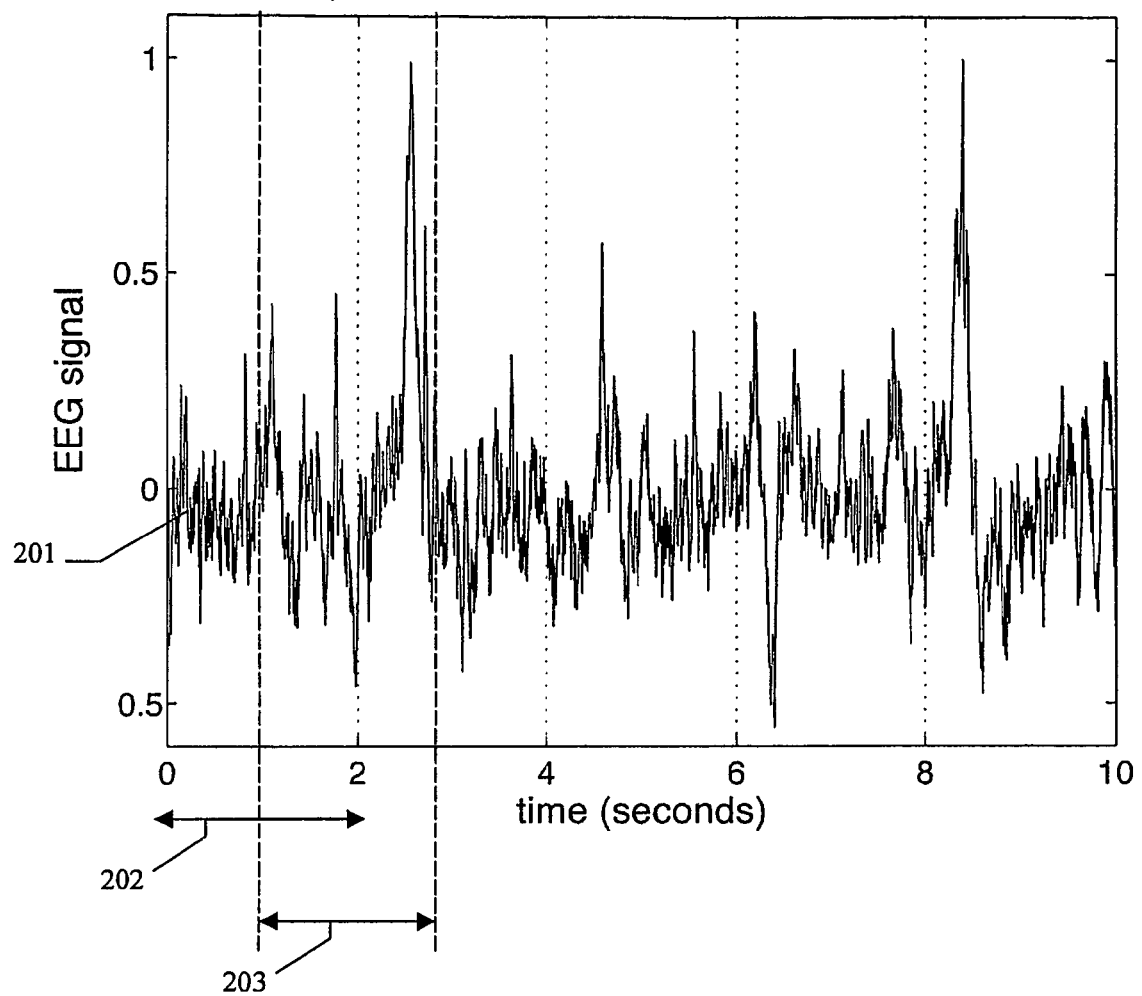
FIG. 10 is an example of an EEG signal typically recorded from a subject over the course of a 10-second interval.

It is preferable that the EEG is analysed as a sequence of overlapping fixed length segments. This technique is further described with reference to FIG. 10. FIG. 10 shows an example of a typical EEG signal 201 recorded from a subject over a period of 10 seconds. To illustrate the preferred sampling technique, it is assumed that recorded EEG signals are digitised and segmented into fixed, overlapping, 2 second segments. The first EEG segment 202 extends from 0 to 2 seconds. The next EEG segment 203 overlaps with the preceding EEG segment (e.g. from 1 to 3 seconds). This process is repeated for all subsequent segments of the EEG signal. This example is based on the assumption that the degree of signal overlap for all EEG segments is 50% of the immediately preceding sample. While this only reflects the best segmenting practice, it is possible to segment the EEG signals into any constant time interval and with any degree of overlap. The EEG signal segment is typically sampled (i.e. digitised) at anywhere between 200 to 500 samples per second.

Referring to FIG. 1, the EEG signal is transmitted as an analog signal via multiple independent electrical connections 103 that connect each electrode 101 to the input ports 104 of an analog filter and amplification device 105. The signals from each electrode, when grouped together, constitute the aggregate EEG signal which is then amplified and filtered in the analog filter and amplification device 105. The analog EEG signal is sent to an analog/digital ("A/D") converter 106, which digitises the filtered analog EEG signal. Preferably, filtering of the digital EEG signal is performed by the analog filter and amplification device 105, which removes any 50 Hz artefacts and other sources of noise that may contaminate subsequent signal analysis. However digital filtering can also be performed by software running on the central processing unit ("CPU") of a personal computer ("PC"). The digitised EEG signal is sent to a PC 107 via a data connection 108, which includes a serial or parallel connection. Upon entering the PC, the digitised EEG signal is sent to the CPU 109 via internal data bus connections. The CPU 109 controls a memory module 110, which may comprise of random access memory ("RAM") components for short-term or temporary storage and recall of data, or a hard disk or another device that provides more permanent storage. The software for processing the digital EEG signal is also stored in either the RAM or hard disk of the memory module.

The system may process the digitised EEG signal on-the-fly, such that an EEG is repeated obtained over consecutive and constant time intervals, and where each time interval may overlap with the immediately preceding time interval as described above. The EEG obtained for each time interval may be temporarily stored in the RAM memory components of the system before it is processed shortly after it has been put in the RAM and removed from the RAM after the EEG for that time interval has been processed. There may be more than one EEG stored in the RAM at any time, which corresponds to the EEGs obtained for different time intervals.

The digitised EEG signal may also be obtained and recorded before it is processed. The digitised EEG signal may be recorded on more permanent forms of storage, such as a hard disk, tape drive or a compact disc ("CD"). The recorded EEG can therefore be processed at any time after it has been recorded or can be used as a reference for comparisons with other EEGs (that may be recorded from the same subject or also from different subjects) at a future point in time.

Referring to FIG. 1, the CPU 109 runs software to perform ARMA modelling on the digital EEG signal and to calculate the 14 ARMA coefficients according to Equation 15 below. This may be done using the "ARMASA Matlab Toolbox" software by P.M.T Broersen (Delft University of Technology), or any of the large number of commercially or freely available ARMA software modelling packages.

Upon determining these 14 coefficients, the CPU 109 uses software, which may be the same software package as described above, to calculate and graphically plot the 8 pole positions on the z-plane for that EEG segment. The software instructs the CPU 109 to send the graphical data generated by the software to a display device 111 controlled by the CPU 109, in which the display device 111 may be connected to the CPU 109 via internal data bus connections. The display device 111 generates a visual representation of the information within the graphical data generated by the software, which may be in the form of a graph or chart as shown in FIGS. 6, 7 8 and 9.

Although FIG. 1 shows that the system may be implemented with the assistance of additional hardware components, it is possible to implement some of the features provided by the hardware using software. For example, with reference to FIG. 1, the functions provided by the analog filter and amplifier 105 and A/D converter 106 can be implemented using software. As such, it is possible to implement the process of filtering and amplifying an analog EEG signal, A/D conversion (digitising the EEG signal), segmentation of the digitised EEG signal, storage of the digitised EEG signal, solving of the 14 ARMA coefficients for each segment of the digitised EEG signal and generating a graphical plot or other visual representation of a single set or consecutive sets of 8 poles derived from one or multiple segment of the digitised EEG signal respectively, as one software package.

Before describing the methods of the invention, it is desirable to explain the theoretical basis of the principles upon which the methods of the invention are based. The alpha rhythm is arguably the most obvious recordable feature of the intact human brain. While the exact basis for its genesis is still controversial it is widely believed that it arises as a consequence of one or more of the following mechanisms:

endogenous or exogenous (thalamic) pacing of cortical neurons;

oscillatory activity generated through the reciprocal interactions of excitatory (pyramidal) and inhibitory (interneuron) cortical neuronal populations; or boundary dependent standing wave generation (Schumann like resonance) due to long range cortico-cortical connectivity.

However none of these mechanisms are sufficient, either separately or taken together, in explaining the physiological genesis of the alpha rhythm.

A theory of alpha electrorhymogenesis (as discussed in Liley et al. Network: Comput. Neural Syst. 13 (2002) 67-113, the contents of which are hereby incorporated in this specification) is based upon a detailed spatially continuous two-dimensional mean field theory of electrocortical activity. Reference is also made to an article entitled *Drug-Induced Modification of System Properties Associated with Spontaneous Human Encephalographic* Activity, (Liley D. T. J. et al. Phys Rev E 68 (2003) 051906), the contents of which are also incorporated herein by cross-reference. According to this theory, the brain acts as a white noise filter to its electrical neural input and the alpha rhythm arises as a result of the filtering of input signals going to the cortex. The filter properties are determined by the bulk (macroscopic/large-scale) anatomical and physiological properties of excitatory and inhibitory cortical neurons.

In this theory, inhibition is conceived as having an important role in determining the properties of the "cortical filter" and thus the spectra of the alpha rhythm generated. In particular the selective modification of the strength of cortical inhibitory action by benzodiazepines, such as alprazolam, is associated with specific changes in the properties of this filter. As such, it is found that the strength and form of the population inhibitory→inhibitory synaptic interactions are the most sensitive determinates of the frequency and damping of the emergent alpha band oscillatory activity. Such behaviour arises principally because local inhibitory→inhibitory and local inhibitory→excitatory loop delays that are associated with physiologically and electroencephalographically plausible alpha activity are longer than the corresponding local (intra-cortical) and long-range (cortico-cortical) excitatory→excitatory loop delays.

This theory differs from other macroscopic continuum theories in that the time course of the unitary inhibitory post-synaptic potential ("IPSP") is described by a third order differential equation. Lower orders are theoretically found to be unable to support any appreciable or widespread alpha band activity.

The principal state variables modelled under this theory are the mean soma membrane potentials of local cortical populations of excitatory and inhibitory neurons. The local field potential, and hence the EEG or electrocorticogram ("ECoG") signal, is regarded as being linearly related to the mean soma membrane potential of the excitatory neurons. This theory can be cast as a set of coupled non-linear one-dimensional partial differential equations that incorporate the major bulk anatomical and physiological features of cortical neurons and includes cable delays, neurotransmitter kinetics and cortico-cortical and intra-cortical connectivities. The spontaneous alpha rhythm is theorized to predominantly arise as a consequence of the local linear properties of the cortex. For this reason in the current formulation spatial effects have been restricted to one dimension.

In accordance with this theory the following non-linear equations (Equations 1, 2, 3 and 4) mathematically represent the brain's electrical activity, as further described in Liley et al. Network: Comput. Neural Syst. 13 (2002) 67-113:

$$\tau \frac{\partial h(x,t)}{\partial t} = h^{rest} - h(x,t) + \bar{\psi}_e(h)I_e(x,t) + \bar{\psi}_i(h)I_i(x,t) \qquad \text{Equation 1}$$

$$\left(\frac{\partial}{\partial t} + \gamma_e\right)^2 I_e(x,t) = \Gamma_e \gamma_e \exp(1)\{N_e^\beta S_e(h_e) + \phi(x,t) + p_e(x,t)\} \qquad \text{Equation 2}$$

$$\left(\frac{\partial}{\partial t} + \gamma_i\right)^2 I_i(x,t) = \Gamma_i \gamma_i \exp(1)\{N_i^\beta S_i(h_i) + p_i(x,t)\} \qquad \text{Equation 3}$$

$$\left(I\frac{\partial}{\partial t} + \bar{v}\Lambda\right)^2 \phi(x,t) - \bar{v}^2 \frac{\partial^2 \phi(x,t)}{\partial x^2} = \bar{v}\Lambda N^\alpha \left(\bar{v}\Lambda + I\frac{\partial}{\partial t}\right) S_e(h_e) \qquad \text{Equation 4}$$

where $h=(h_e,h_i)^T$, $h^{rest}=(h_e^{rest},h_i^{rest})^T$, $I_e=(I_{ee},I_{ei})$, $I_i=(I_{ie},I_{ii})^T$, $N_{ee}^\beta=(N_{ee}^\beta,N_{ei}^\beta)^T$, $N_i^\beta=(N_{ie}^\beta,N_{ii}^\beta)^T$, $N^\alpha=(N_{ee}^\alpha,N_{ei}^\alpha)^T$, $\phi=(\phi_e,\phi_i)^T$, $\Lambda=\text{diag}(\Lambda_{ee},\Lambda_{ei})$, $\tau=\text{diag}(\tau_e,\tau_i)$, $\Psi_j(h)=\text{diag}(\psi_j(h_e),\psi_j(h_i))$, $p_e=(p_{ee},p_{ei})^T$, $p_i=(p_{ie},p_{ii})^T$ and I is the identity matrix, with:

$$S_j(h_j)=S_j^{max}(1+\exp[-\sqrt{2}(h_j-\bar{\mu}_j)/\hat{\sigma}_j])^{-1} \qquad \text{Equation 5}$$

$$\psi_j(h_{j'})=(h_j^{eq}-h_{j'})/|h_j^{eq}-h_j^{rest}| \qquad \text{Equation 6}$$

where j, j'=e, i.

Table 1 is a table which shows the ranges of all the theoretical parameters (i.e. the numerical values of all anatomical and physiological parameters) that are used by the above equations to generate parameter sets that give rise to stable physiological alpha activity. The ranges in Table 1 refer to the intervals from which uniform parameter deviates were generated.

TABLE 1

Typical parameter values

| Symbol | Definition | Typical Value | Range | Units |
|---|---|---|---|---|
| e, i | Excitatory, inhibitory | — | — | — |
| $h_e$, $h_i$ | Mean soma membrane potential of e and i neurons | — | — | — |
| $h_e^{rest}$, $h_i^{rest}$ | Mean resting membrane potential of e and i neurons | −60, −60 | — | mV |
| $h_e^{eq}$, $h_i^{eq}$ | Mean reversal potential associated with excitation or inhibition | 0, −70 | — | mV |
| $N^\alpha_{ee}$, $N^\alpha_{ei}$ | Mean total number of connections that a cell of type e, i receives from excitatory cells via cortico-cortical fibers | 4000, 2000 | 2000-5000, 1000-3000 | — |
| $N^\beta_{ee}$, $N^\beta_{ei}$ | Mean total number of connections that a cell of type e, i receives from excitatory cells via intracortical fibers | 3034, 3034 | 2000-5000, 2000-5000 | — |
| $N^\beta_{ie}$, $N^\beta_{ii}$ | Mean total number of connections that a cell of type e, i receives from inhibitory cells via intracortical fibers | 536, 536 | — | — |
| $\tau_e$, $\tau_i$ | Effective passive membrane time constant | 0.01, 0.01 | 0.005-0.15, 0.005-0.15 | s |
| $\kappa = \Lambda_{ee} = \Lambda_{ei}$ | Characteristic scale of e→e, e→i cortico-cortical fibers | 0.4 | 0.1-1.0 | $cm^{-1}$ |
| $v$ | Mean cortico-cortical conduction velocity | 700 | 1-1000 | $cm\ s^{-1}$ |

TABLE 1-continued

Typical parameter values

| Symbol | Definition | Typical Value | Range | Units |
|---|---|---|---|---|
| $\Gamma_e, \Gamma_i$ | Effective excitatory, inhibitory postsynaptic potential peak amplitude | 0.4, 0.8 | —, 0.1-2 | mV |
| $\gamma_e, \gamma_i$ | Effective excitatory, inhibitory postsynaptic potential rate constant | 300, 65 | 100-500, 10-200 | $s^{-1}$ |
| $\bar{\mu}_e, \bar{\mu}_i$ | Excitatory, inhibitory population thresholds | −50, −50 | −60-0, −60-0 | mV |
| $S_e^{max}, S_i^{max}$ | Excitatory, inhibitory population mean maximal firing rates | 100, 100 | — | Hz |
| $p_{ee}, p_{ei}$ | Excitatory input to excitatory, inhibitory cells | 0, 0 | — | Hz |
| $p_{ie}, p_{ii}$ | Inhibitory input to excitatory, inhibitory cells | 0, 0 | — | Hz |
| $\hat{\sigma}_e, \hat{\sigma}_i$ | Standard deviation for firing threshold in excitatory, inhibitory populations | 5, 5 | — | mV |

Non-Linear Equations 1 to 6 need to be transformed into their linear equivalent in order to be solved. To determine theoretically whether the alpha rhythm can be understood in terms of a white noise fluctuation spectrum the above equations are linearized about spatially homogeneous singular points. For a given set of parameters these singular points can be obtained by setting all spatial and temporal derivatives to zero and solving for $h_e$. In general these singular points, $h_e^*$, are solutions to the following equation:

$$F(h_e(q), q) = 0 \quad \text{Equation 7}$$

where q represents a vector of model parameters and $F(\bullet)$ is obtained from Equations 1, 2, 3 and 4.

Linearizing Equations 1, 2, 3 and 4 about the spatially homogenous singular point $h_e^*$ and transforming to the Fourier domain yields the following equation:

$$H_e(k, \omega) = \frac{\exp(1)\Gamma_e\gamma_e\eta_e}{\tau_e} \frac{N(k, \omega: q)}{D(k, \omega: q)} P(k, \omega) \quad \text{Equation 8}$$

$$= G_e(k, \omega: q) P(k, w) \quad \text{Equation 9}$$

where k and ω are wave number and angular frequency respectively. Loosely speaking, k specifies the reciprocal of the characteristic physical scale over which oscillations of frequency ω occur. $H_e(k,\omega)$ is the Fourier transform of the mean soma membrane potential of excitatory neurons $h_e(x,t)$. $h_e(x,t)$ has been shown to be proportional to the surface recorded electrical activity, the EEG, of the brain. The function $G_e$ is the electrocortical transfer function, q is a vector of parameters and $P(k,\omega)$ represents the spatio-temporal form of cortical input.

The terms $N(k,\omega,q)$ and $D(k,\omega,q)$ in Equation 8 can be expressed as the following Equations 10 and 11, where the corresponding parameters for the parameter vector 'q' in Equation 8 has now been explicitly identified in Equations 10 and 11.

$$N(k, \omega) = \quad \text{Equation 10}$$
$$\{(i\omega + \gamma_i)^2(i\omega + \eta_i/\tau_i) - w_{ii}N_{ii}^\beta Q_i\}\{(\kappa + i\omega/\upsilon)^2 + k^2\}$$

$$D(k, \omega) = \{(i\omega + \gamma_i)^2(i\omega + \eta_i/\tau_i) - w_{ii}N_{ii}^\beta Q_i\} \quad \text{Equation 11}$$
$$[\{(\kappa + i\omega/\upsilon)^2 + k^2\}(i\omega + \eta_e/\tau_e)(i\omega + \gamma_e)^2 - w_{ee}$$
$$Q_e(N_{ee}^\alpha \kappa(\kappa + i\omega/\upsilon) + N_{ee}^\beta\{(\kappa + i\omega/\upsilon)^2 + k^2\})] - w_{ei}$$
$$w_{ie}N_{ie}^\beta Q_e Q_i(N_{ei}^\alpha \kappa(\kappa + i\omega/\upsilon) + N_{ei}^\beta\{(\kappa + i\omega/\upsilon)^2 + k^2\})$$

$$w_{j'j} = \exp(1)\Gamma_{j'}\gamma_{j'}\eta_{j'}\psi_{j'}(h_j^*)/(\tau_{j'}\eta_j) \quad \text{Equation 12}$$

$$\eta_j = 1 + \exp(1)\Gamma_e(N_{ej}^\alpha + N_{ej}^\beta)S_e(h_e^*)/(\gamma_e|h_e^{eq} - h_j^{rest}|) + \quad \text{Equation 13}$$
$$\exp(1)\Gamma_i N_{ij}^\beta S_i(h_i^*)/(\gamma_i|h_i^{eq} - h_j^{rest}|)$$

$$Q_j = \partial S_j/\partial h_j|_{h_j = h_j^*} \quad \text{Equation 14}$$

From Equation 10, the highest order in ω is 5, which corresponds to the moving average order of the ARMA model. From Equation 11, the highest order in ω is 8, which corresponds to the auto-regressive order of the ARMA model.

Equations 8, 10 and 11 can be rewritten in a summary form as Equations 12, 13 and 14, as shown above.

Equation 14 can be rewritten as a difference equation, as shown in Equation 15, which represents a linear time invariant discrete time system:

$$y[n] = -\sum_{k=1}^{8} a_k y[n-k] + \sum_{k=0}^{5} b_k u[n-k] \quad \text{Equation 15}$$

where y[n] is the digitised EEG signal, u[n] is a Gaussian white noise process and $a_k$ and $b_k$ are coefficients to be determined for a given EEG time series. More specifically, u[n] represents a sequence of normally (Gaussian) distributed uncorrelated random variables and in the context of the analysis herein is used to represent the driving input to the fixed order ARMA model. From a physiological perspective it corresponds to the input the cortex receives which is assumed to be so complicated to be indistinguishable from white noise.

Equation 15 represents an (8,5) order ARMA model, where the specific values of the orders are derived from Equations 10 and 11. The 14 coefficients from the ARMA model can be determined using any of the large number of commercially or freely available ARMA software modelling packages, such as the ARMASA Matlab Toolbox software by P.M.T Broersen (Delft University of Technology).

To understand how the 14 coefficients so obtained can be used to measure brain function, Equation 15 is rewritten in the z-domain by taking the z-transform. Thus Equation 15 can be equivalently written in the z-domain as:

$$Y(z) = \frac{\sum_{k=0}^{5} b_k z^{-k}}{1 + \sum_{k=1}^{8} a_k z^{-k}} U(z) = \frac{B(z)}{A(z)} U(z) \quad \text{Equation 16}$$

Solutions to $A(z)=0$ in Equation 16 will give the system poles and solutions to $B(z)=0$ in Equation 16 will give the system zeros. In general, these solutions are complex with $|z|<1$. The maximum power of the denominator in Equation 16 suggests that there are 8 unique system poles. The eight complex solutions to $A(z)=0$ are then plotted on the z-plane.

Figure 2:
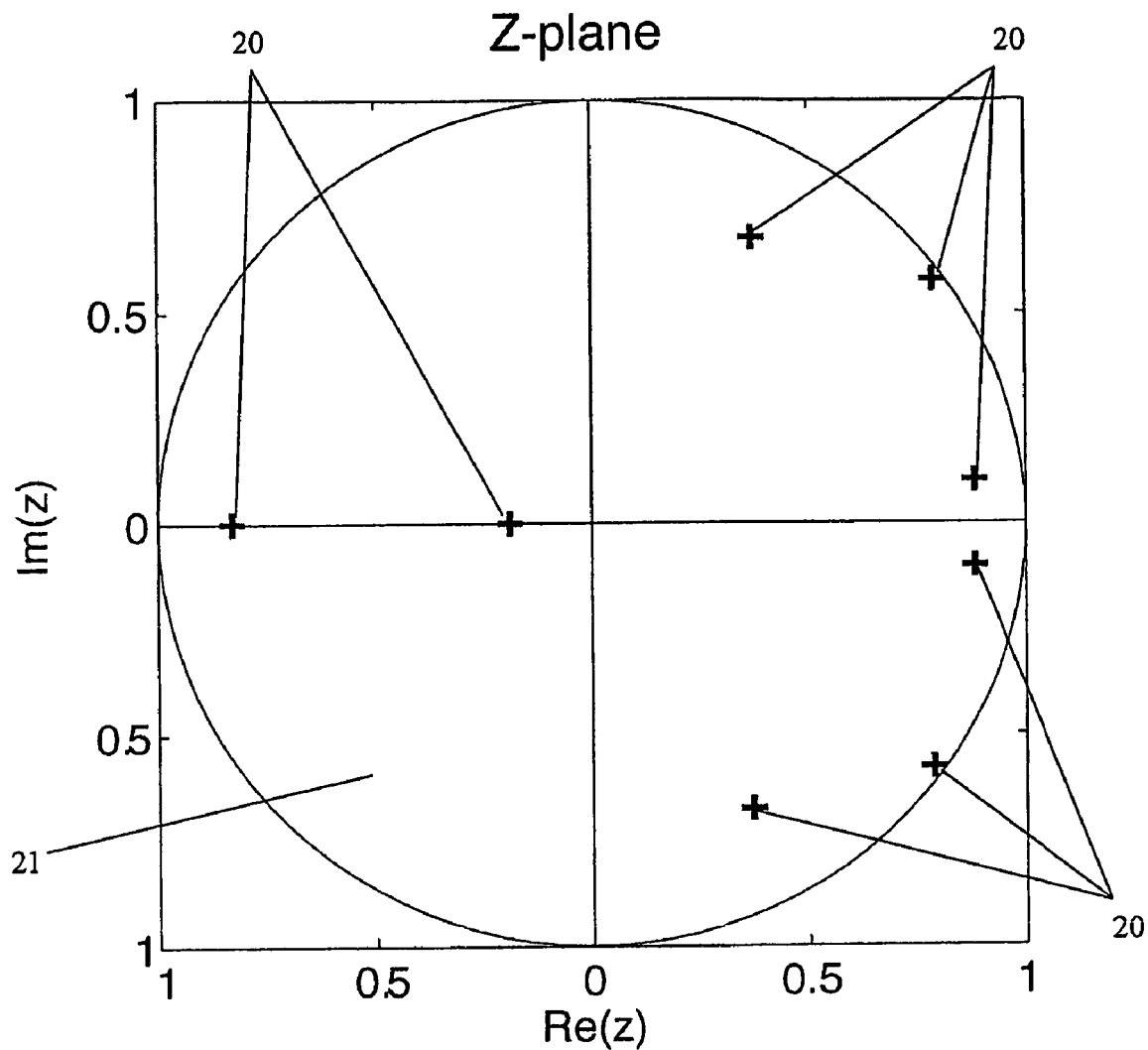
FIG. 2 is a diagram showing an example of the 8 poles derived from one segment of an EEG signal plotted onto the z-plane.
Figure 3:
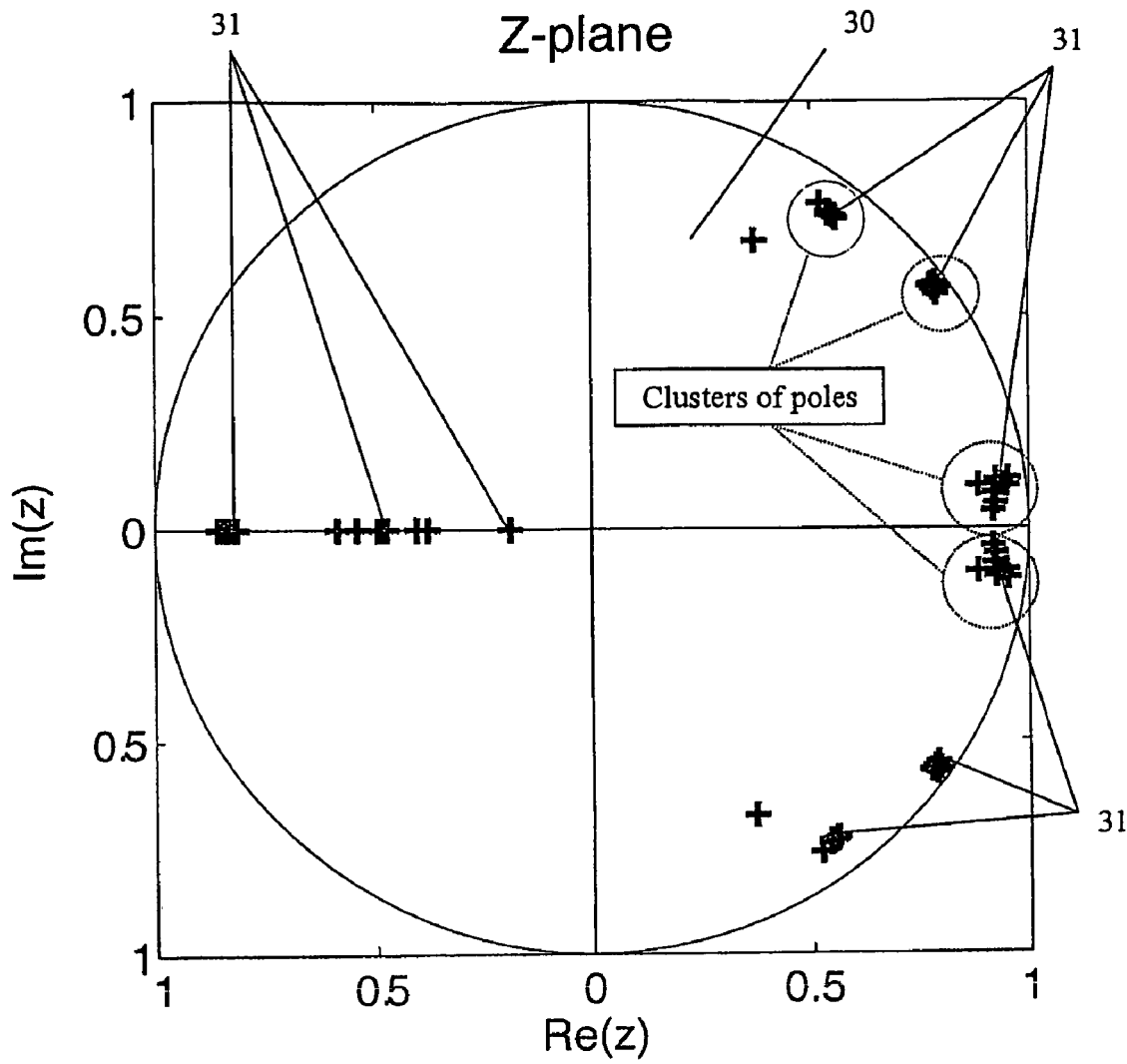
FIG. 3 is a diagram showing an example of the cumulative positions of the 8 poles derived from several segments of an EEG signal plotted onto the same z-plane.

The location of the eight poles derived from Equation 16 represent the state of the brain as determined by the EEG signals recorded over the particular time interval. With reference to FIG. 2, the set of eight poles from one EEG segment 20 is plotted on the z-plane 21. With reference to FIG. 3, the application of Equation 15 to subsequent segments of EEG from the entire EEG sample allows further sets of eight poles 31 to be determined and plotted onto the same z-plane 30 that contains the poles plotted from the preceding EEG samples 31.

Figure 4:
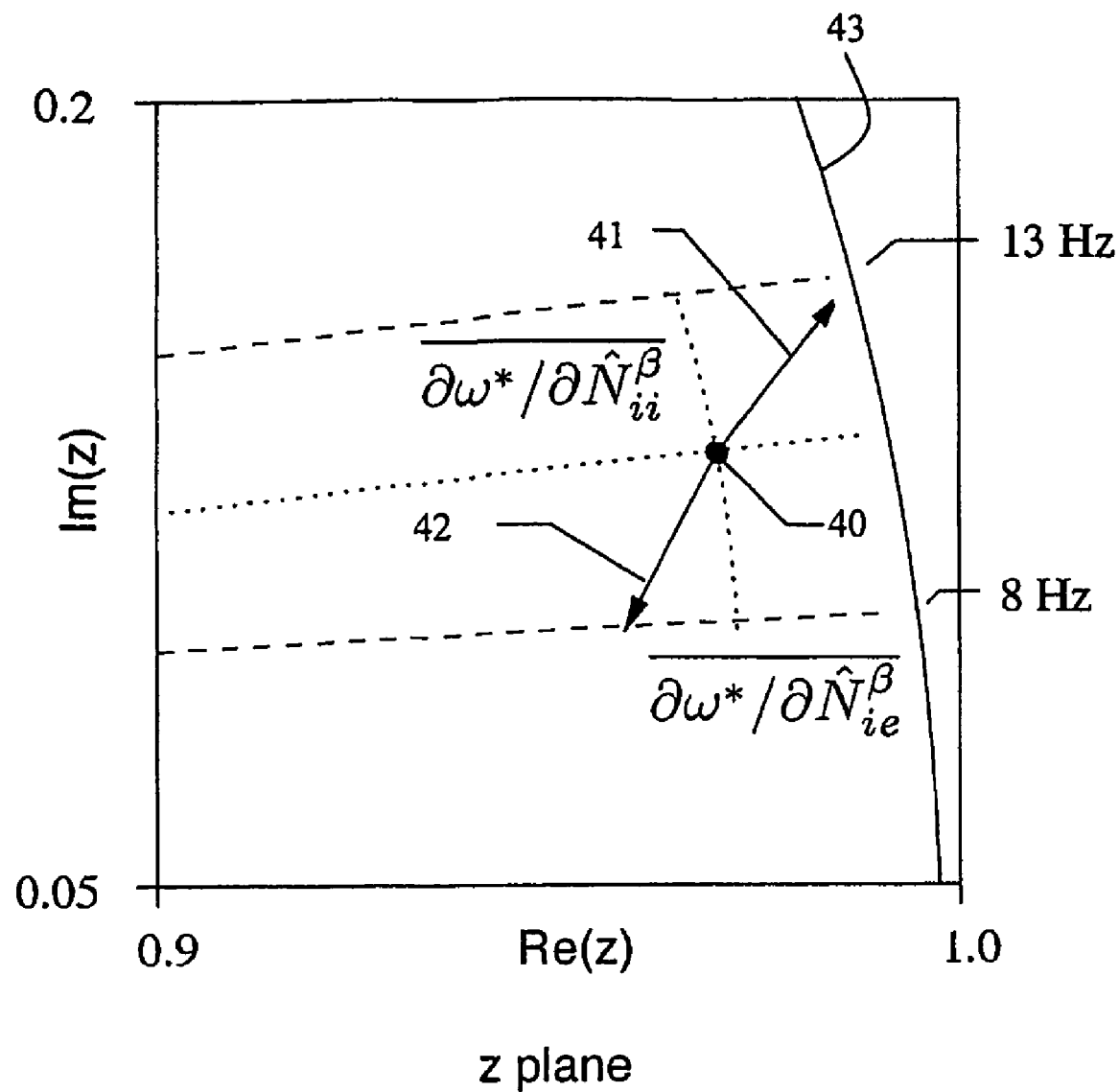
FIG. 4 is a diagram showing the schematic representation on the z-plane of the predicted effects of increasing the strength of neuronal population inhibitory→inhibitory and inhibitory→excitatory synaptic interactions.

Theoretically, the results in FIG. 3 can be interpreted with reference to FIG. 4. FIG. 4 is the schematic representation of the predicted effects of increasing the strength of neuronal population inhibitory→inhibitory and inhibitory→excitatory synaptic interactions. The filled circle 40 approximately represents the theoretical loci of the dominant poles associated with electroencephalographically plausible eyes-closed alpha activity. In other words, the filled circle 40 represents the most weakly damped pole, which can be thought of as corresponding to the most dominant oscillatory component making up the human alpha rhythm. For any recording of human alpha rhythm, a frequency analysis using a Fourier transform would reveal the approximate frequency of this dominant pole or the dominant oscillatory component. The arrows 41 and 42 in FIG. 4 indicate the mean predicted direction of the motion of these poles in response to increases in inhibitory→inhibitory $$\overline{(\partial \omega^* / \partial \hat{N}_{ii}^\beta)}$$

41 and inhibitory→excitatory $$\overline{(\partial \omega^* / \partial \hat{N}_{ie}^\beta)}$$

42 synaptic strength.

Figure 5:
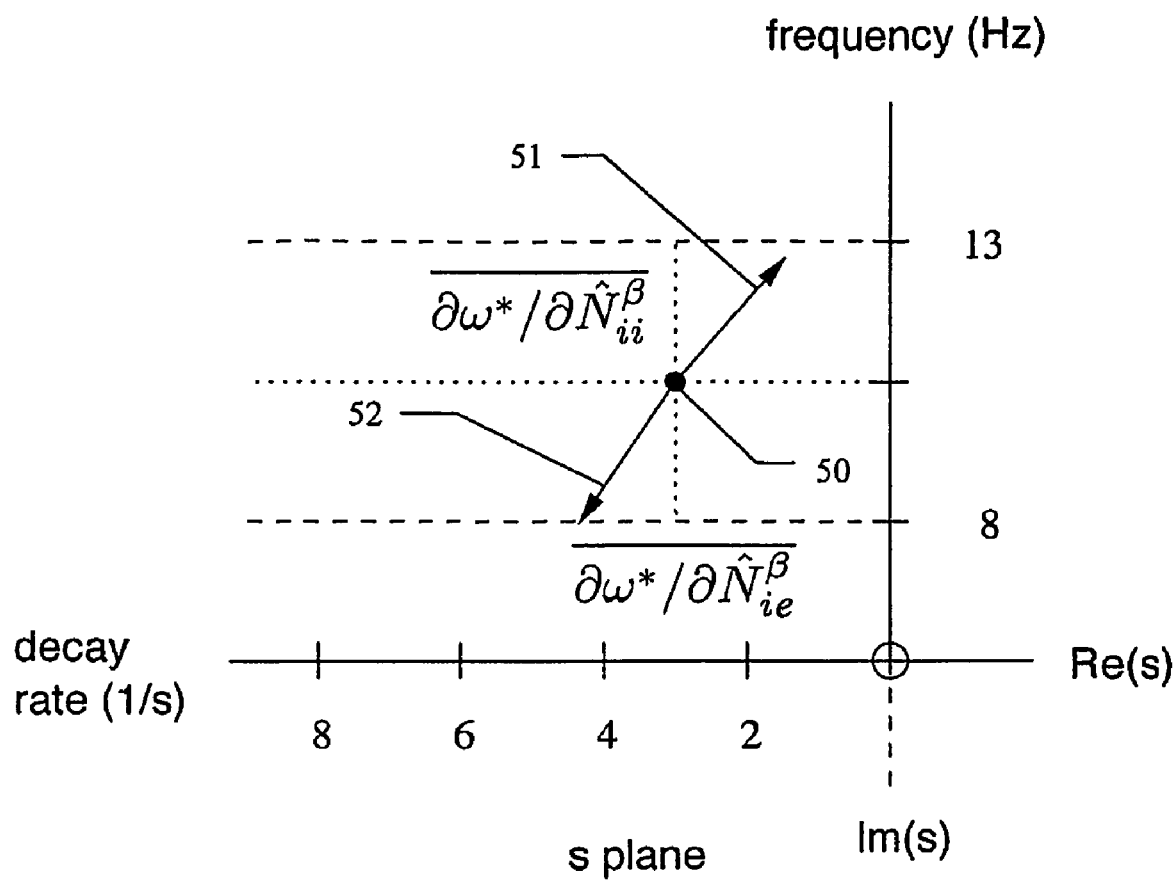
FIG. 5 is a diagram showing the schematic representation on the s-plane (which can also be referred to as the Laplace or Fourier plane) of the predicted effects of increasing the strength of neuronal population inhibitory→inhibitory and inhibitory→excitatory synaptic interactions.

FIG. 5 shows the same information as FIG. 4 as plotted on the s-plane (Laplace or Fourier plane) rather than the z-plane. The filled circle 50 approximately represents the theoretical loci of the dominant poles associated with electroencephalographically plausible eyes-closed alpha activity. The arrows 51 and 52 in FIG. 5 indicate the mean predicted direction of the motion of these poles in response to increases in inhibitory→inhibitory $$\overline{(\partial \omega^* / \partial \hat{N}_{ii}^\beta)}$$

51 and inhibitory→excitatory $$\overline{(\partial \omega^* / \partial \hat{N}_{ie}^\beta)}$$

52 synaptic strength.

The decay rate is related to the sharpness of the resonance of the dominant oscillatory component in the recorded EEG signal. Increasing decay rates would correspond to the broadening of the alpha resonance in human EEG recordings. In FIG. 5, the arrow 51 represents an increasing decay rate as it moves away from the filled circle 50, which represents a single pole. The arrow 52 represents a decreasing decay rate as it moves away from the pole 50. In FIG. 4, the closer that the pole 40 moves to the boundary of the unit circle 43 the smaller the decay, whereas the further the pole moves from the boundary 43 the larger the decay. Referring to FIG. 4, an anti-clockwise motion of the pole 40 implies that the pole's frequency increases, whereas a clockwise motion of the pole implies that the frequency decreases. Thus, according to this theory of alpha rhythm generation, changes in the decay rate(s) associated with the dominant oscillatory component gives information in addition to that which can be obtained using the Fourier analysis of human EEG.

Figure 6:
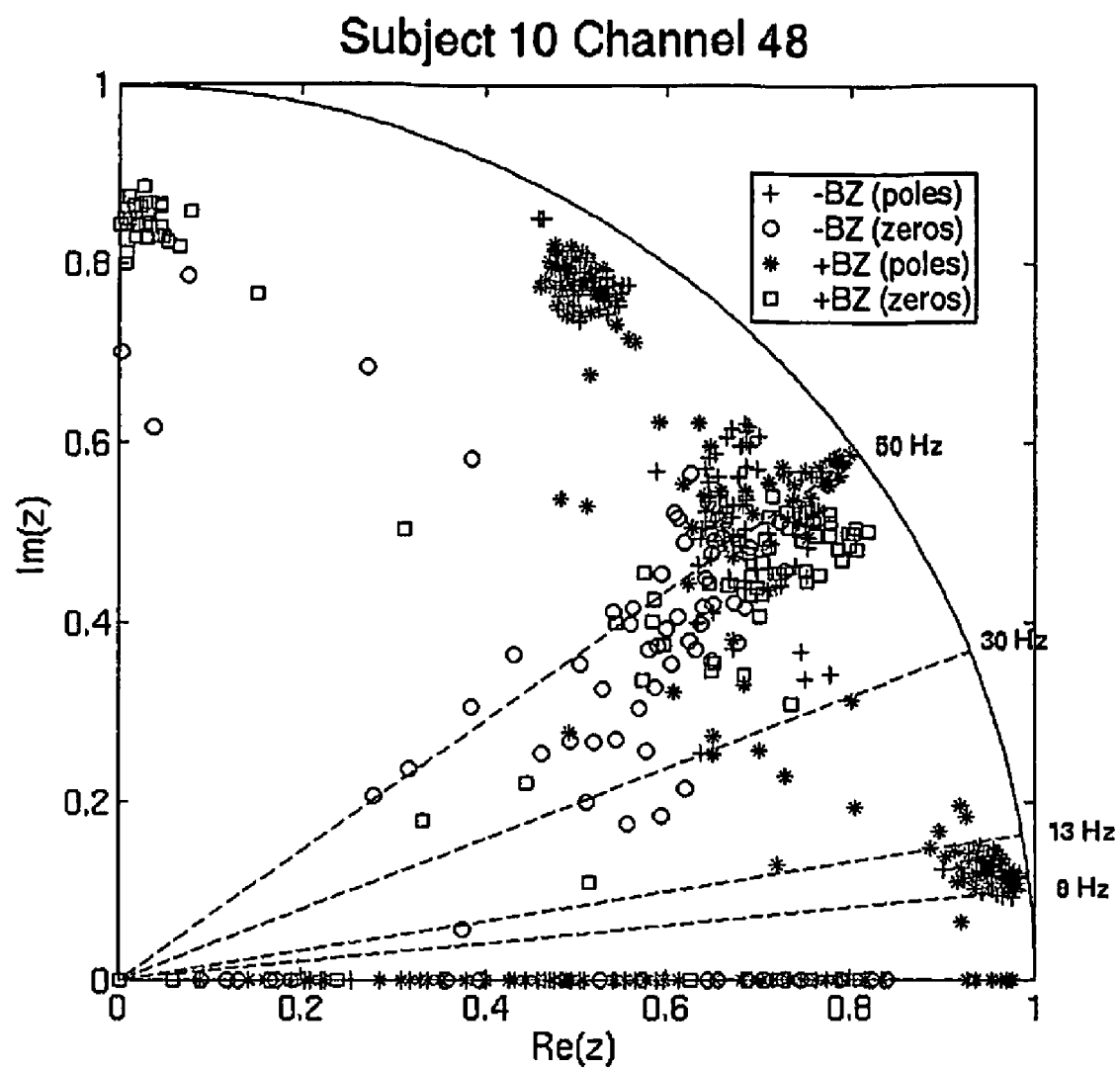
FIG. 6 is an example of the upper right quadrant of the z-plane in a pole-zero plot for a typical subject before (as shown by the "−BZ" poles and zeros) and after (as shown by the "+BZ" poles and zeros) the administration of the benzodiazepine, alprozolam, on the subject.
Figure 7:
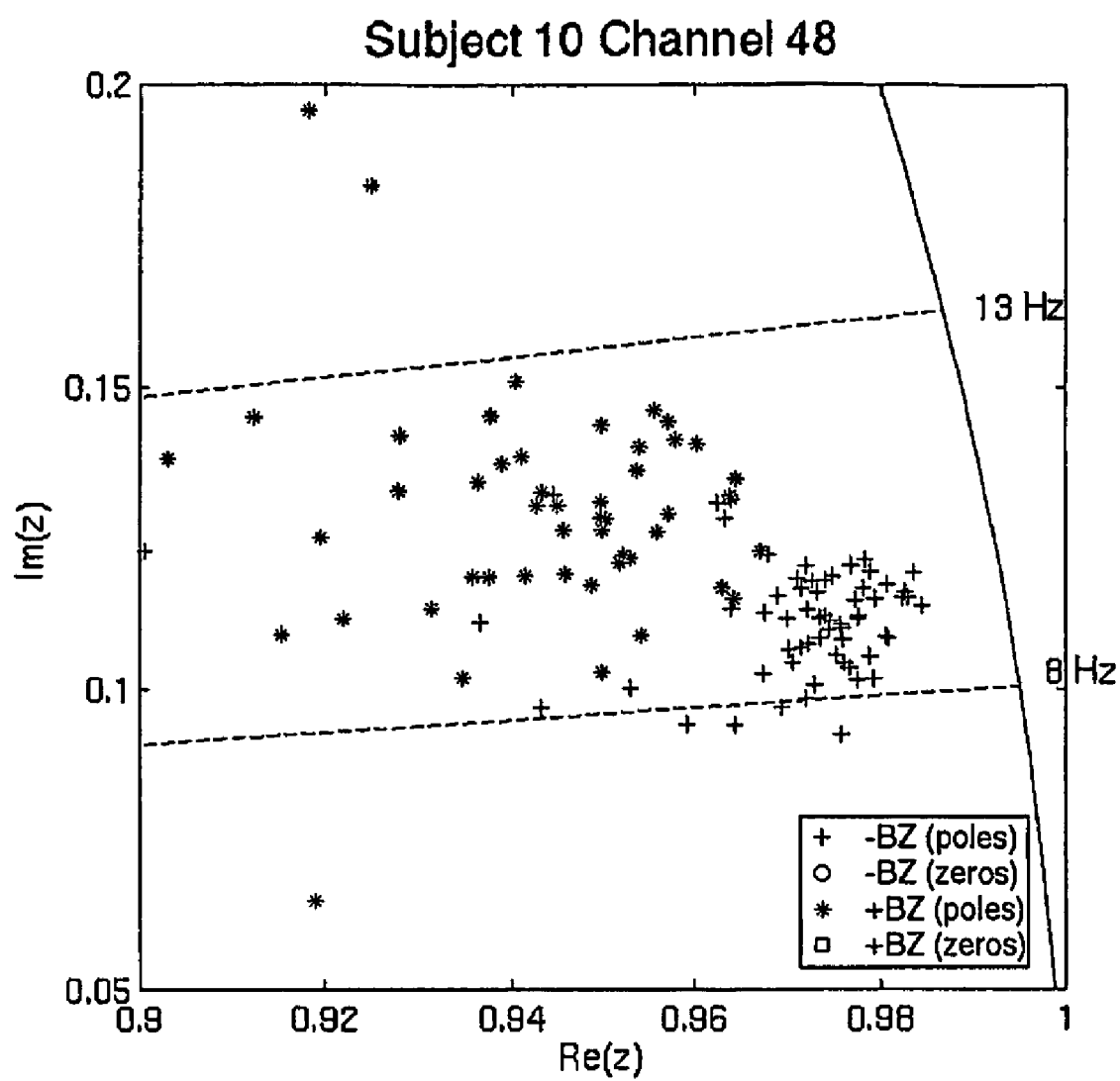
FIG. 7 is an example of a detailed view of a region of the upper right quadrant of the z-plane between 8 to 13 Hz of a pole-zero plot for a typical subject before (as shown by the "−BZ" poles and zeros) and after (as shown by the "+BZ" poles and zeros) the administration of the benzodiazepine, alprozolam, on the subject.
Figure 8:
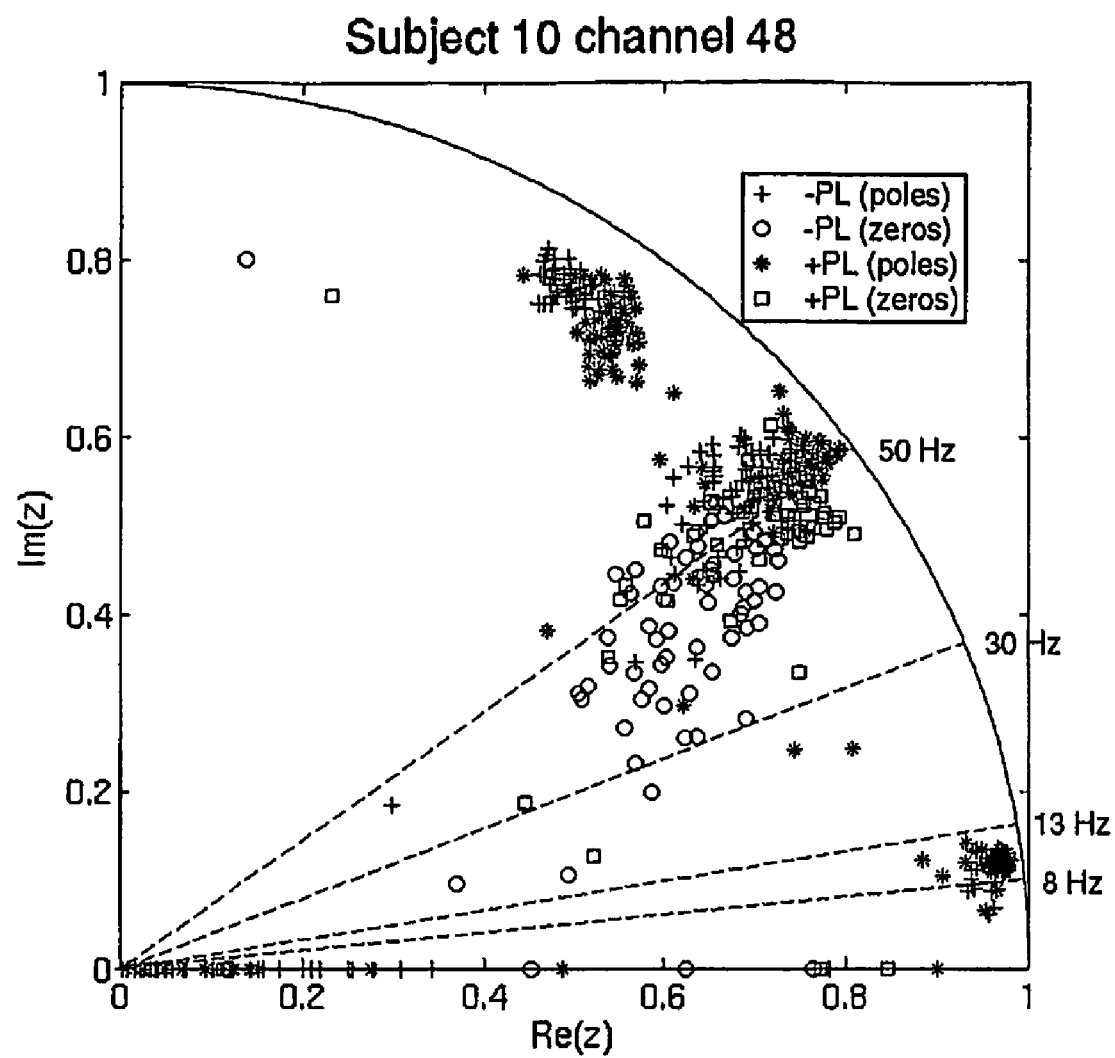
FIG. 8 is an example of the upper right quadrant of the z-plane in a pole-zero plot for a typical subject before (as shown by the "−PL" poles and zeros) and after (as shown by the "+PL" poles and zeros) the administration of a placebo on the subject.
Figure 9:
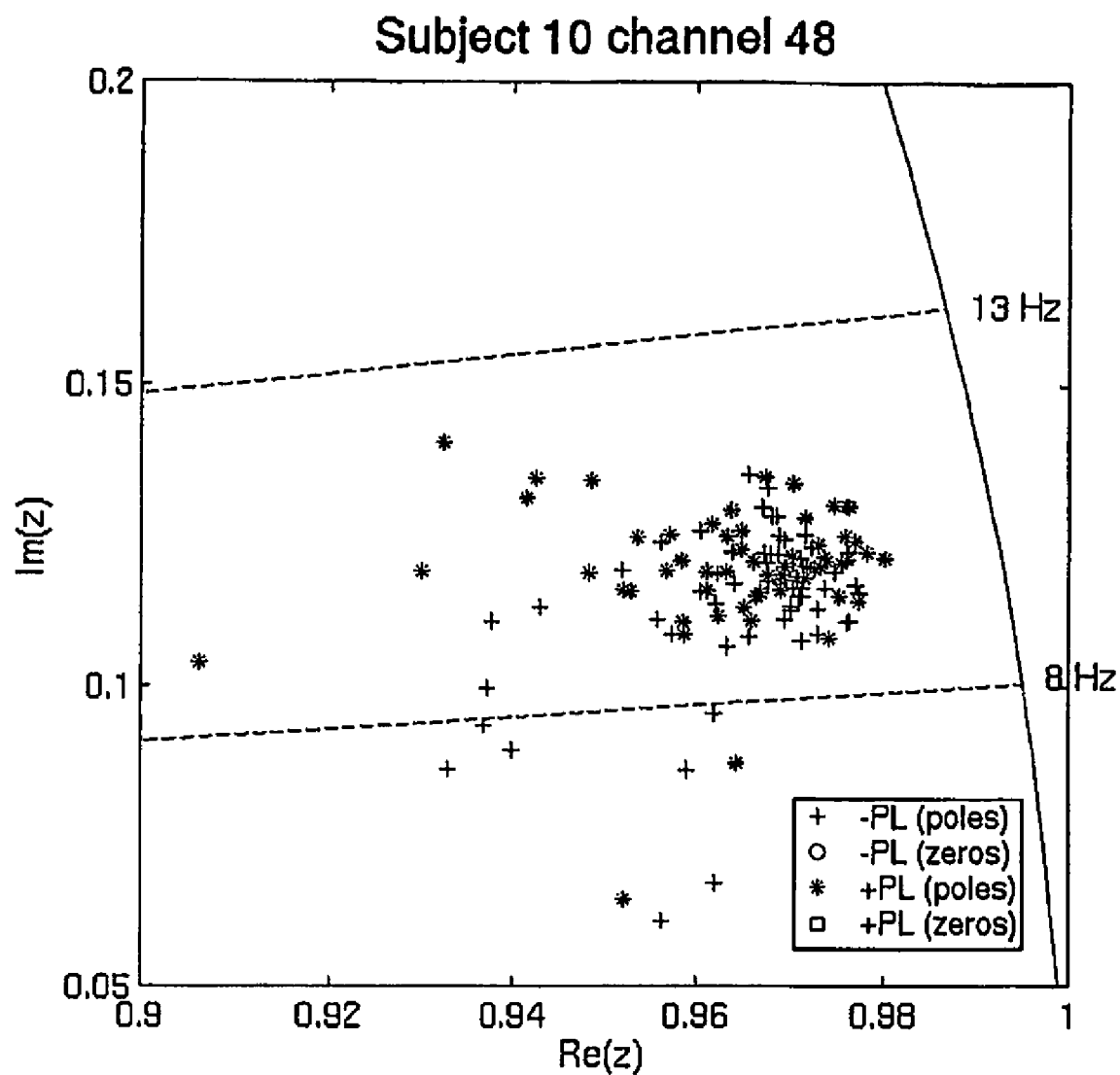
FIG. 9 is an example of a detailed view of a region of the upper right quadrant of the z-plane between 8 to 13 Hz of a pole-zero plot for a typical subject before (as shown by the "−PL" poles and zeros) and after (as shown by the "+PL" poles and zeros) the administration of a placebo on the subject.

FIGS. 6 and 7 show the position of the poles and zeros in a pole-zero plot for a typical subject before (as shown by the "−BZ" poles and zeros) and after (as shown by the "+BZ" poles and zeros) the administration of the benzodiazepine as an oral dose of alprazolam. A similar pole-zero plot for a typical subject is shown in FIGS. 8 and 9 before (as shown by the "−PL" poles and zeros) and after (as shown by the "+PL" poles and zeros) the administration of a placebo. Where they apply in FIGS. 6, 7, 8 and 9, poles are indicated with "+" or "*" and zeros indicated with "○" or "□".

FIGS. 7 and 9 show in more detail the region of the z-plane, from FIGS. 6 and 8 respectively, corresponding to a region of 8-13 Hz activity. The important features to note are:
  (i) the distinct groupings of poles and zeros populating the z-plane;
  (ii) distinct populations of poles having frequencies lying in the range 8-13 Hz;
  (iii) clear differences between the location of the centroids of the alpha poles before (as indicated by the "−BZ" poles and zeros in FIGS. 6 and 7) and following (as indicated by the "+BZ" poles and zeros in FIGS. 6 and 7) administration of the benzodiazepine; and
  (iv) insubstantial differences between the location of the alpha poles before (as indicated by the "−PL" poles and zeros in FIGS. 8 and 9) and following (as indicated by the "+PL" poles and zeros in FIGS. 8 and 9) administration of the placebo.

It is evident from FIG. 7 that the variability of the alpha pole location after the ingestion of the benzodiazepine is more pronounced that in the other three conditions. Compared to the placebo condition, as shown in FIG. 9, it can be seen that alprazolam causes a significant shift in the most weakly damped pole constituting the alpha rhythm, such that its corresponding frequency and damping both increased. In the absence of any other poles this implies that alprazolam causes the alpha spectrum to shift to the right and broaden, as shown in FIGS. 7 and 9. Variations in the mean location of these clusters of poles and their distribution will result as a consequence of ongoing normal behaviour, disease progression and state, or pharmacological or therapeutic interventions or manipulations. As such, the mean location of the poles is a measure of brain state and the movement of the mean location of these poles is a measure of changes in brain state or function.

Figure 11:
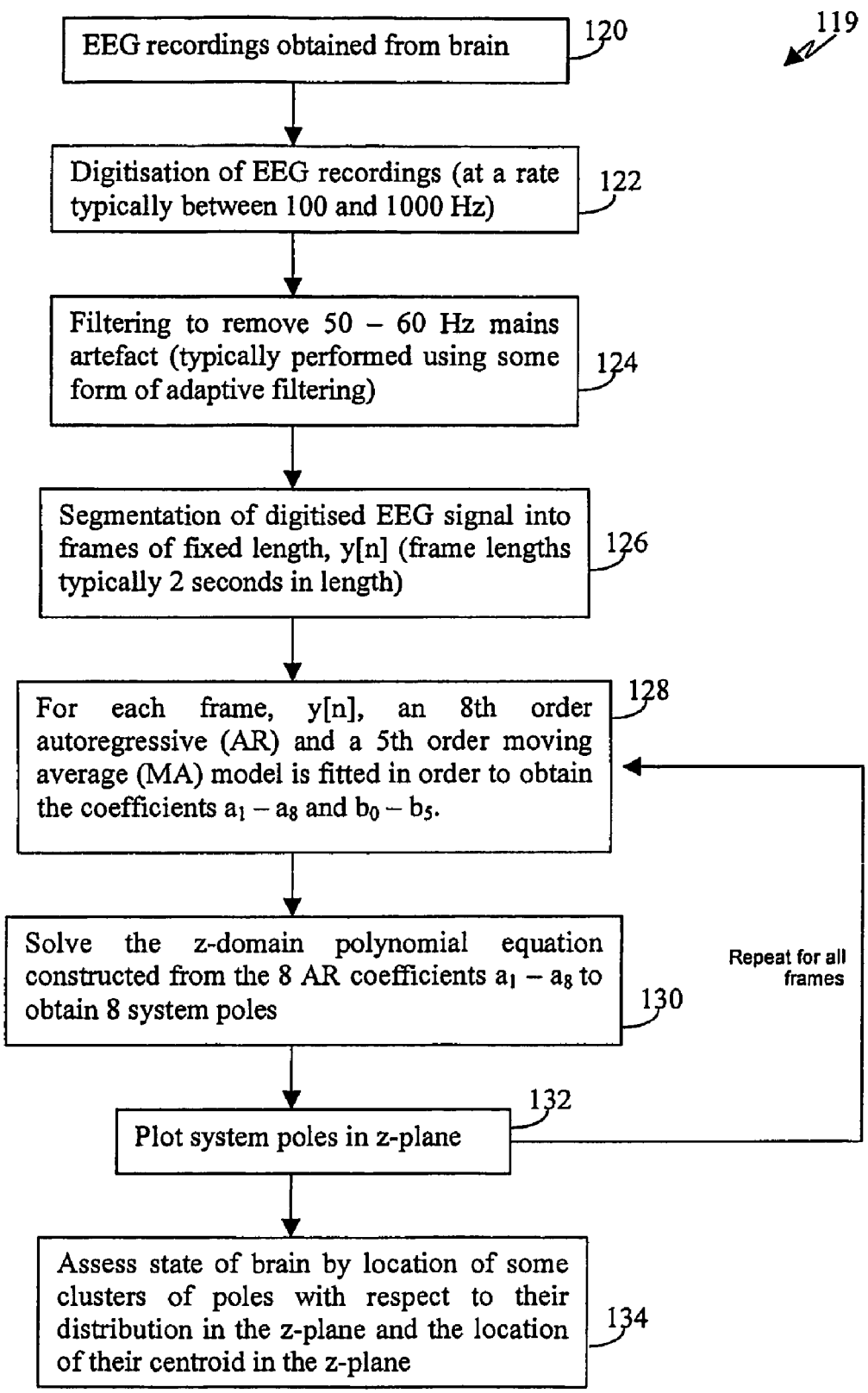
FIG. 11 is a schematic flowchart of the significant steps in an embodiment of the method of the invention.

FIG. 11 is a flowchart 119 which diagrammatically illustrates some of the important steps in the method described above. Briefly, step 120 represents obtaining EEG signals from the brain of the subject. Step 122 represents digitisation as carried out by the converter 106. Step 124 represents digital filtering which is carried out in the PC 107. Step 126 represents segmentation of the EEG signal which is also carried out in the PC 107. Step 128 represents computation carried out by the CPU 109 in order to obtain the coefficients $A_1$-$A_8$ and $B_0$-$B_5$. Step 130 represents the step of solving the z-domain polynomial equation in order to obtain system poles and step 132 represents plotting the system poles in the z-plane. These poles can be displayed on the display device 111. Steps 128, 130 and 132 are repeated for each of the frames.

Step 134 represents the step of assessment of the results by reference to the distribution of clusters of poles in the z-plane. This step would normally be carried out by an operator.

Figure 12:
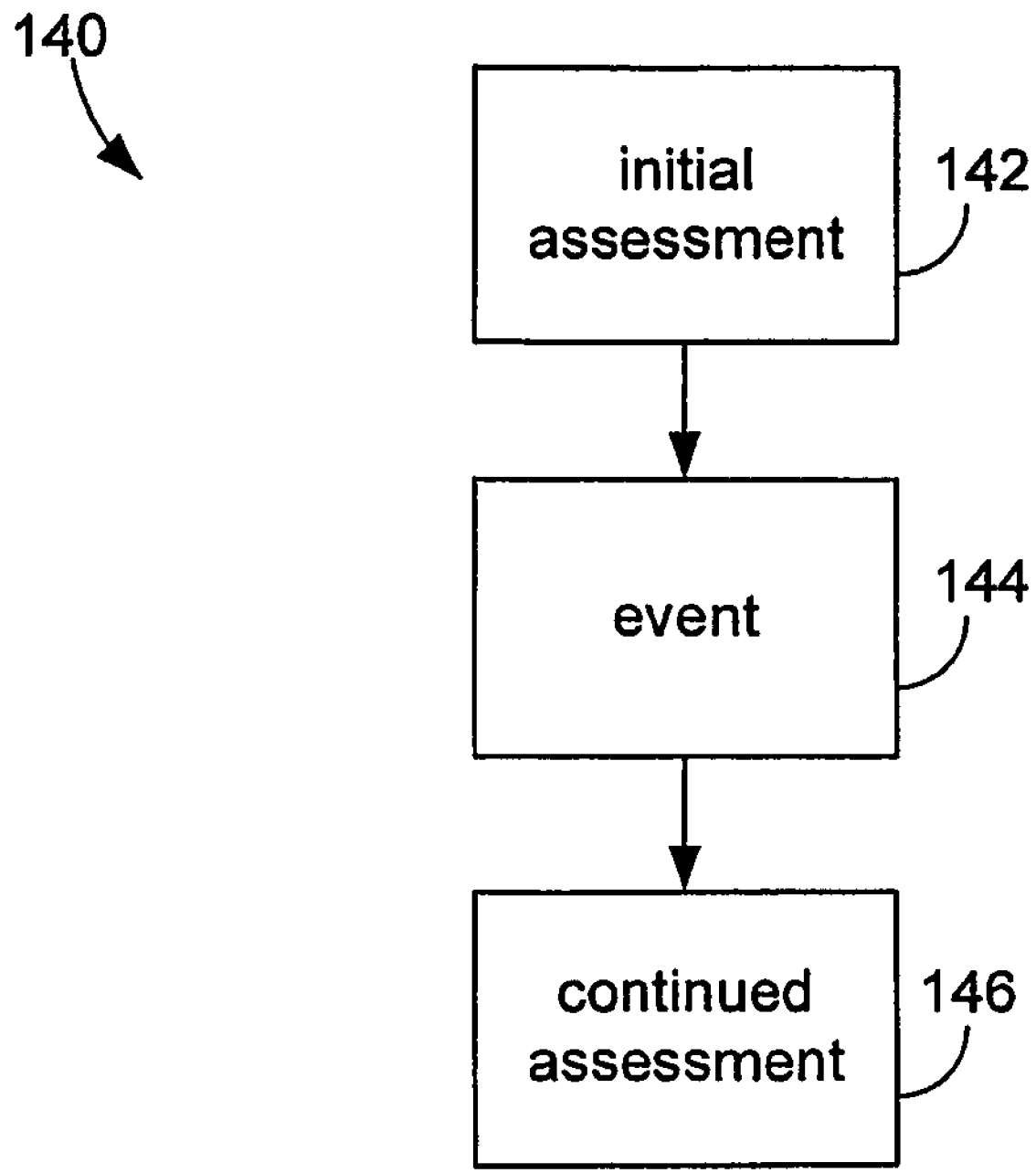
FIG. 12 is a simplified flowchart showing significant steps of a further embodiment of the invention.

FIG. 12 shows a flowchart 140 which shows some of the important steps of embodiments of methods of the invention. The flowchart 140 includes a step 142 which is regarded as an initial assessment of the brain state of a subject. The step 142 may comprise all of the steps 120 to 134 of the flowchart 119. In other words the operator would carry out an initial assessment of the subject prior to carrying out of an event, as indicated by step 114. The event 114 may be the administration of a cognitively active pharmaceutical agent to a subject being tested or the administration of an anaesthetic to the patient. Step 146 represents continuation of the monitoring of the results after the event 146 so as to determine the effect of the event. The continued assessment step 146 typically includes all of the steps 120 to 134 of the flowchart 119 of FIG. 11. For instance where the event is the administration of a dose of a cognitively active pharmaceutical agent, the step 146 enables assessment of the effect which the agent has on the brain of the subject. This assessment is, of course, objective rather than subjective, in accordance with the principles of the invention. Where the step 144 is the administration of an anaesthetic to the patient, the step 146 enables the continued monitoring of the clusters of poles by the anaesthetist or an operator in order to monitor the state of anaesthetic depth of the patient so that the anaesthetist is able to control the rate of application of anaesthetic to the subject. Again, in accordance with the principles of the invention, this assessment is done objectively rather than subjectively.

The reference to any prior art in this specification is not and should not be taken as an acknowledgement or any form of suggestion that prior art forms part of the common general knowledge in Australia.

Many modifications will be apparent to those skilled in the art without departing from the spirit and scope of the invention.

The invention claimed is:

1. A method for assessing brain state comprising:
analysing mammalian brain electroencephalogram (EEG) recordings using an eighth order autoregressive and fifth order moving average discrete time equation;
obtaining a z-domain equation by taking a z-transform for said eighth order autoregressive and fifth order moving average discrete time equation;
determining, using a processing unit, poles and zeroes in the solution of the z-domain equation; and
plotting the poles onto the complex plane; and
displaying positions of the poles.

2. The method as claimed in claim 1 further comprising a system having means for analysing mammalian brain electroencephalogram (EEG) recordings using an eighth order autoregressive and fifth order moving average discrete time equation.

3. A method of assessing the state of a mammalian brain including the steps of:
obtaining an electroencephalogram (EEG) from the brain;
(ii) digitising the EEG to define a digitised EEG data signal;
(iii) segmenting the EEG data signal into time frames of fixed length, y[n];
(iv) approximating, using a processing unit, each digitised time frame by a first equation:

$$y[n] = -\sum_{k=1}^{8} a_k y[n-k] + \sum_{k=0}^{5} b_k u[n-k]$$

where $a_k$ and $b_k$ are coefficients to be determined for the EEG data signal, y[n] represents the digitized EEG data signal, and u[n] represents a Gaussian white noise process;
(v) solving the first equation to determine coefficients $a_1$ to $a_8$ and $b_0$ to $b_5$;
(vi) performing a z-transform, using a processing unit, on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

$$B(z) = \sum_{k=0}^{5} b_k z^{-k}$$

(vii) substituting each of the values of the coefficients into the z-domain equation;
(viii) solving A(z)=0 for z in the second equation to determine the poles;
(ix) determining, using a processing unit, the positions of the poles in the complex plane;
(x) repeating steps (iv) to (ix) for each frame in the sample to determine clusters of poles in the complex plane; and
(xi) displaying the position and distribution of at least some of said clusters of poles in the complex plane.

4. A method as claimed in claim 3 including the step of filtering the EEG to remove noise signals therefrom prior to carrying out step (iii).

5. A method as claimed in claim 3, wherein said EEG is obtained and recorded before it is processed.

6. A method as claimed in claim 5 including the step of filtering the EEG to remove noise signals therefrom prior to carrying out step (iii).

7. A method as claimed in claim 3, wherein the step of step (x) is repeated continuously to track the motion of the poles from each segment.

8. A method as claimed in claim 3, wherein the step of step (xi) includes the steps:
- (xi)(a) taking the centroid of the poles for each cluster of poles; and
- (xi)(b) monitoring and comparing the movement of said centroids.

9. A method as claimed in claim 8 including the step of:
- (xi)(c) analysing the statistical variability of the poles in said clusters of poles.

10. The method as claimed in claim 3 wherein steps (i)-(xi) are performed by a computer having a computer readable medium with computer program instructions stored thereon.

11. A method as claimed in claim 3 wherein step (xi) is used to assess the state of vigilance or alertness of a subject.

12. A method as claimed in claim 3 wherein step (xi) is used to assess the state of sleep of a subject.

13. A method as claimed in claim 3 wherein step (xi) is used to assess the state of anaesthesia of a subject.

14. A method of assessing the efficacy of an intervention in a mammalian brain including the steps of:
- (i) obtaining an electroencephalogram (EEG) from the brain;
- (ii) digitising the EEG to define a digitised EEG data signal;
- (iii) segmenting the EEG data signal into time frames of fixed length, y[n];
- (iv) approximating, using a processing unit, each digitised time frame by a first equation:

$$y[n] = -\sum_{k=1}^{8} a_k y[n-k] + \sum_{k=0}^{5} b_k u[n-k]$$

where $a_k$ and $b_k$ are coefficients to be determined for the EEG data signal, y[n] represents the digitized EEG data signal, and u[n] represents a Gaussian white noise process;
- (v) solving the first equation to determine coefficients $a_1$ to $a_8$ and $b_0$ to $b_5$;
- (vi) performing a z-transform, using a processing unit, and on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

$$B(z) = \sum_{k=0}^{5} b_k z^{-k}$$

- (vii) substituting each of the values of the coefficients into the z-domain equation;
- (viii) solving A(z)=0 for z in the second equation to determine the poles;
- (ix) determining, using a processing unit, the positions of the poles in the complex plane;
- (x) repeating steps (iv) to (ix) for each frame in the sample to determine first clusters of poles in the complex plane; and
- (xi) administering an intervention to the brain;
- (xii) repeating steps (i) to (x) at least once in order to obtain second clusters of poles in the complex plane;
- (xiii) displaying the positions of at least some of the first and second clusters of poles; and
- (xiv) assessing the efficacy of the intervention by reference to movement of at least some of said first and second clusters of said displayed poles in the complex plane.

15. A method of assessing the state of a mammalian brain including the steps of:
- (i) obtaining a first electroencephalogram (EEG) from the brain;
- (ii) digitising the EEG to define a digitised EEG data signal;
- (iii) segmenting the EEG data signal into time frames of fixed length, y[n];
- (iv) approximating, using a processing unit, each digitised time frame by a first equation:

$$y[n] = -\sum_{k=1}^{8} a_k y[n-k] + \sum_{k=0}^{5} b_k u[n-k]$$

where a $a_k$ and $b_k$ are coefficients to be determined for the EEG data signal, y[n] represents the digitized EEG data signal, and u[n] represents a Gaussian white noise process;
- (v) solving the first equation to determine coefficients $a_1$ to $a_8$ and $b_0$ to $b_5$;
- (vi) performing a z-transform, using a processing unit, on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

-continued $$B(z) = \sum_{k=0}^{5} b_k z^{-k}$$

(vii) substituting each of the values of the coefficients into the z-domain equation;
(viii) solving A(z)=0 for z in the second equation to determine the poles;
(ix) determining, using a processing unit, positions of the poles in the complex plane;
(x) repeating steps (iv) to (ix) for each frame in the sample to determine clusters of poles in the complex plane;
(xi) obtaining a second EEG from said brain at a later time;
(xii) repeating steps (ii) to (xi) in relation to the second EEG at least once;
(xiii) displaying the positions of at least some of the poles derived from the first and second EEGs respectively in the complex plane; and
(xiv) assessing the state of the brain by reference to movement of at least some of said clusters of poles.

16. A method as claimed in claim 15, wherein said first and second EEG is obtained and recorded before it is processed.

17. A method as claimed in claim 15, wherein said EEG, or said first and second EEG, is obtained and recorded in its entirety for processing at a later point in time.

18. A method as claimed in claim 15, wherein said EEG, or said first and second EEG, is each repeatedly obtained over consecutive and constant time intervals.

19. A method as claimed in claim 18, wherein a said time interval may overlap with an immediately preceding time interval.

20. A method as claimed in claim 15, wherein the step of step (xv) includes the steps of:
(xv)(a) taking the centroid of the poles for each cluster of poles; and
(xv)(b) monitoring and comparing the movement of said centroids.

21. A method as claimed in claim 20 including the step of:
(xv)(c) analysing the statistical variability of the poles in said clusters of poles.

22. A system for displaying the activity of a mammalian brain, the system including:
a plurality of electrodes for picking up EEG signals from the brain;
digitising means for converting the EEG signals to a digitised EEG data signal;
computing means for:
(i) segmenting the EEG data signal into time frames of fixed length, y[n];
(ii) approximating each digitised time frame by a first equation:

$$y[n] = -\sum_{k=1}^{8} a_k y[n-k] + \sum_{k=0}^{5} b_k u[n-k]$$

where $a_k$ and $b_k$ are coefficients to be determined for the EEG data signal, y[n] represents the digitized EEG data signal, and u[n] represents a Gaussian white noise process;
(iii) solving the first equation to determine coefficients $a_1$ to $a_8$ and $b_0$ to $b_5$;
(iv) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

$$B(z) = \sum_{k=0}^{5} b_k z^{-k}$$

(v) substituting each of the values of the coefficients into the z-domain equation;
(vi) solving A(z)=0 for z in the second equation to determine the poles;
(vii) determining the positions of the poles in the complex plane;
(viii) repeating steps (ii) to (vii) for each frame in the sample to determine clusters of poles in the complex plane; and
display means for displaying the position and distribution of at least some of said clusters of poles in the complex plane.

23. A system for assessing the efficacy of an intervention in a mammalian brain, the system including:
a plurality of electrodes for picking up EEG signals from the brain;
digitising means for converting the EEG signals to a digitised EEG data signal;
computing means for:
(i) segmenting the EEG data signal into time frames of fixed length, y[n];
(ii) approximating each digitised time frame by a first equation:

$$y[n] = -\sum_{k=1}^{8} a_k y[n-k] + \sum_{k=0}^{5} b_k u[n-k]$$

where $a_k$ and $b_k$ are coefficients to be determined for the EEG data signal, y[n] represents the digitized EEG data signal, and u[n] represents a Gaussian white noise process;
(iii) solving the first equation to determine coefficients $a_1$ to $a_8$ and $b_0$ to $b_5$;
(iv) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

$$B(z) = \sum_{k=0}^{5} b_k z^{-k}$$

(v) substituting each of the values of the coefficients into the z-domain equation;
(vi) solving $A(z)=0$ for z in the second equation to determine the poles;
(vii) determining the positions of the poles in the complex plane;
(viii) repeating steps (ii) to (vii) for each frame in the sample to determine first clusters of poles in the complex plane and, after administration of an intervention to the brain;
(ix) repeating steps (i) to (vii) at least once in order to obtain second clusters of poles in the complex plane; and
display means for displaying the position and distribution of at least some of said first and second clusters of poles in the complex plane in order to assess the efficacy of the intervention.

24. A system for displaying the activity of a mammalian brain, the system including:
a plurality of electrodes for picking up EEG signals from the brain;
digitising means for converting the EEG signals to a digitised EEG data signal;
computing means for:
(i) segmenting the EEG data signal into time frames of fixed length, y[n];
(ii) approximating each digitised time frame by a first equation:

$$y[n] = -\sum_{k=1}^{8} a_k y[n-k] + \sum_{k=0}^{5} b_k u[n-k]$$

where $a_k$ and $b_k$ are coefficients to be determined for the EEG data signal, y[n] represents the digitized EEG data signal, and u[n] represents a Gaussian white noise process;
(iii) solving the first equation to determine coefficients $a_1$ to $a_8$ and $b_0$ to $b_5$;
(iv) performing a z-transform on the first equation to obtain a second, z-domain equation:

$$Y(z) = \frac{\sum_{k=0}^{5} b_k z^{-k}}{1 + \sum_{k=1}^{8} a_k z^{-k}} U(z) = \frac{B(z)}{A(z)} U(z)$$

where
Y[z] represents y[u] in the z-domain and U(z) represents u[n] in the z-domain, and:

$$A(z) = 1 + \sum_{k=1}^{8} a_k z^{-k}$$

$$B(z) = \sum_{k=0}^{5} b_k z^{-k}$$

(v) substituting each of the values of the coefficients into the z-domain equation;
(vi) solving $A(z)=0$ for z in the second equation to determine the poles;
(vii) determining positions of the poles in the complex plane;
(viii) repeating steps (ii) to (vii) for each frame in the sample to determine clusters of poles in the complex plane;
(ix) obtaining a second EEG from said brain at a later time; and
(x) repeating steps (i) to (viii) in relation to the second EEG at least once; and
display means for displaying the position and distribution of at least some of said clusters of poles in the complex plane derived from the first and second EEGs.

* * * * *